(12) United States Patent
Englmann et al.

(10) Patent No.: US 8,816,146 B2
(45) Date of Patent: Aug. 26, 2014

(54) ORGANOMETALLIC COMPLEXES AS CATALYST PRECURSORS FOR SELECTIVE OLEFIN DIMERIZATION AND PROCESSES THEREFOR

(75) Inventors: Tanja Englmann, Immenreuth (DE); Christine Denner, Gefrees (DE); Helmut G. Alt, Bayreuth (DE); Roland Schmidt, Bartlesville, OK (US); Matthias Dötterl, Bayreuth (DE)

(73) Assignee: Phillips 66 Company, Houston, TX (US)

( * ) Notice: Subject to any disclaimer, the term of this patent is extended or adjusted under 35 U.S.C. 154(b) by 424 days.

(21) Appl. No.: 12/829,075

(22) Filed: Jul. 1, 2010

(65) Prior Publication Data

US 2011/0004040 A1 Jan. 6, 2011

Related U.S. Application Data

(60) Provisional application No. 61/222,445, filed on Jul. 1, 2009.

(51) Int. Cl.
*C07C 2/22* (2006.01)

(52) U.S. Cl.
USPC ........... 585/513; 585/502; 585/510; 585/511; 585/520; 585/521

(58) Field of Classification Search
USPC .......... 585/502, 510, 511, 512, 513, 520, 521
See application file for complete search history.

(56) References Cited

U.S. PATENT DOCUMENTS 3,647,883 A * 3/1972 Dubeck et al. ................ 585/511
5,281,679 A 1/1994 Jejelowo et al.

(Continued)

FOREIGN PATENT DOCUMENTS

CN 1463959 A * 12/2003 ................ C07C 2/32
CN 1510014 A * 7/2004 ................ C07C 2/08

(Continued)

OTHER PUBLICATIONS

Walas, "Chemical Reactors" in Perry's Chemical Engineer's Handbook, 7th ed., 1997, McGraw-Hill, available on-line at www.knovel.com on Mar. 1, 2001.*

(Continued)

*Primary Examiner* — In Suk Bullock
*Assistant Examiner* — Bradley Etherton
(74) *Attorney, Agent, or Firm* — Gardere Wynne Sewell LLP; Chris P. Perque; Teresa J. Lechner-Fish

(57) ABSTRACT

Methods for dimerizing alpha-olefins utilizing immobilized buffered catalysts wherein a buffered ionic liquid is mixed with an organometallic complex of the formula:

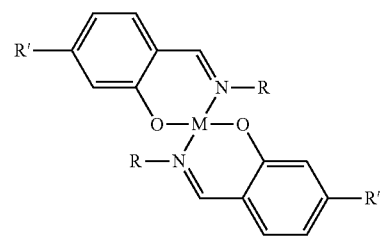

where M is selected from the group of Ti, Zr, Hg, Ni, and V and R and R' are selected from the group consisting of hydrogen, alkyl, aryl, alkenyl, alkynyl, alkyloxy, substituted aryl, and halogens, are provided.

25 Claims, 5 Drawing Sheets

(56) References Cited

U.S. PATENT DOCUMENTS

| | | | |
|---|---|---|---|
| 6,291,733 B1 * | 9/2001 | Small et al. | 585/512 |
| 6,531,555 B2 * | 3/2003 | Whiteker | 526/161 |
| 6,911,410 B2 | 6/2005 | Lecocq et al. | |
| 7,109,284 B2 * | 9/2006 | Ishii et al. | 526/352 |
| 2003/0224927 A1 | 12/2003 | Shih | |
| 2008/0146469 A1 | 6/2008 | Sato et al. | |

FOREIGN PATENT DOCUMENTS

| | | | |
|---|---|---|---|
| JP | 2006342106 A | 12/2006 | |
| WO | WO 9847616 A1 * | 10/1998 | B01J 31/30 |

OTHER PUBLICATIONS

Carlini, et al., "Ethylene Oligomerization by Novel Catalysts Based on Bis(salicylaldiminate) Nickel (II) Complexes and Organoaluminum Compounds" in Appl. Catal. A: General, 231 (2002) 307-320—month unknown.*

Kim, et al., "Ethylene Oligomerization to Low-Carbon Linear Alpha-Olefins by Structure Modulated Phenoxy-imine Nickel (II) Complexes Combined with Aluminum Sesquichloride" in Appl. Catal. A: General, 287 (2005) 98-107—month unknown.*

Mehnert, "Supported ionic Liquid Catalysts" in Chem. Eur. J., 2005, 11, 50-56—month unknown.*

Machine Translation of CN 1463959 A—dated Aug. 2012.*

Machine Translation of CN 1510014 A—dated Aug. 2012.*

Carlini, et al., "Ethylene Oligomerization by Novel Catalysts Based on Bis(salicylaldiminate)Nickel (II) Complexes and Organoaluminum Compounds" in Appl. Catal. A: General, 231 (2002) 307-320—month unknown.*

Kim, et al.("Ethylene Oligomerization to Low-Carbon Linear Alpha-Olefins by Structure Modulated Phenoxy-imine Nickel(II) Complexes Combined with Aluminum Sesquichloride" in Appl. Catal. A: General, 287 (2005) 98-107—month unknown.*

Mehnert ("Supported ionic Liquid Catalysts" in Chem. Eur. J., 2005, 11, 50-56—month unknown.*

Machine Translation of CN 1,463,959.—retrieved Aug. 2012.*

Machine Translation of CN 1,510,014,—retrieved Aug. 2012.*

International Search Report issued Aug. 27, 2010 for PCT/US2010/40850.

International Written Opinion issued Aug. 27, 2010 for PCT/US2010/40850.

International Preliminary Report on Patentability issued Jan. 4, 2012 for PCT/US2010/040850.

* cited by examiner

ORGANOMETALLIC COMPLEXES AS CATALYST PRECURSORS FOR SELECTIVE OLEFIN DIMERIZATION AND PROCESSES THEREFOR

CROSS REFERENCE TO RELATED APPLICATIONS

This application claims priority to U.S. Provisional Application No. 61/222,445, filed Jul. 1, 2009.

FEDERALLY SPONSORED RESEARCH STATEMENT

Not applicable.

REFERENCE TO MICROFICHE APPENDIX

Not applicable.

FIELD OF THE INVENTION

The invention relates to processes for dimerizing alkenes.

BACKGROUND OF THE INVENTION

Dimerization of olefins is well known and industrially useful. Further, the use of transition metals to catalyze olefin dimerization and oligomerization is also known.

Use of ionic liquids for dimerization and oligomerization of olefins is also well known. In the broad sense, the term ionic liquids includes all molten salts, for instance, sodium chloride at temperatures higher than 800° C. Today, however, the term "ionic liquid" is commonly used for salts whose melting point is relatively low (below 100° C.). One of the earlier known room temperature ionic liquids was [EtNH$_3$]+ [NO$_3$] (m.p. 12° C.), the synthesis of which was published in 1914. Much later, series of ionic liquids based on mixtures of 1,3-dialkylimidazolium or 1-alkylpyridinium halides and trihalogenoaluminates, initially developed for use as electrolytes, were to follow. One property of the imidazolium halogenoaluminate salts was that they were tuneable, i.e., viscosity, melting point and the acidity of the melt could be adjusted by changing the alkyl substituents and the ratio of imidazolium or pyridinium halide to halogenoaluminate. Imidazolium halogenoaluminate salts exhibit moisture sensitivity and, depending on the ratio of aluminum halide, Lewis acidic or Lewis basic properties. Ionic liquids with 'neutral', weakly coordinating anions such as hexafluorophosphate ([PF$_6$]$^-$) and tetrafluoroborate ([BF$_4$]$^-$) have also been used as alternatives to imidazolium halogenoaluminate salts. [PF$_6$]$^-$ and [BF$_4$]$^-$ based ionic liquids are generally highly toxic. Yet another anion for use in ionic liquids is bistriflimide [(CF$_3$SO$_2$)$_2$N]$^-$, which does not exhibit the toxicity of [PF$_6$]$^-$ and [BF$_4$]$^-$ anions. Ionic liquids with less toxic cations are also known, including those with compounds like ammonium salts (such as choline) being used in lieu of imidazole.

Ionic liquids have found use as a catalyst in various chemical reactions. For example, Lewis acidic ionic liquids have been used as a catalyst to alkylate aromatic hydrocarbons, such as the alkylation of benzene with ethylene. In such processes, the ionic liquid itself serves as the catalyst, and the catalyst is neither buffered nor immobilized on a support. Ionic liquids have also been used in processes for making high viscosity polyalphaolefins using an oligomerization catalyst including an aluminum halide or alky-aluminum halides, and alkyl-substituted imidazolium halide or pyridinium halide. In such processes, the ionic liquid itself again serves as the catalyst and preferentially forms high-viscosity polyalphaolefins due to the lack of buffering.

Processes utilizing immobilized ionic liquids are also known. For example, immobilized ionic liquids may be prepared by functionalizing a support prior to contact with or forming the ionic liquid. Such known immobilized ionic liquids however are not buffered and therefore preferentially form high viscosity polyolefins. Again, in such systems, the ionic liquid itself functions as the catalyst.

Although all of the above methods are known and used in the synthesis of olefins, what is needed in the art is an improved synthetic method that allows for easy separation of the product. Especially in the case of olefin dimerizations, which usually yield liquids with relatively low viscosities or even gaseous olefins, the application of supported systems allows the use of fixed bed reactors and is superior to batch oligomerization, obviating the need for further product separation. In addition, the catalytically active surface may be maximized by use of high surface support materials, which optimizes the catalytic performance.

SUMMARY OF THE INVENTION

Some embodiments of the invention provide a process for the dimerization of alpha-olefins including: (a) modifying a support material containing —OH groups with an alkylaluminum compound to form a modified support material; (b) mixing an ionic liquid having a melting point below about 70° C. with a buffer to form a buffered ionic liquid; (c) mixing the buffered ionic liquid with an organometallic complex of the formula:

where M is selected from the group of Fe, Ti, Zr, Ni, and V, and R and R' are selected from the group consisting of hydrogen, alkyl, aryl, alkenyl, alkynyl, alkyloxy, substituted aryl, and halogens to form a buffered ionic liquid/catalyst complex; (d) mixing the buffered ionic liquid/catalyst; and (e) mixing the immobilized buffered catalyst with one or more alpha-olefins.

In certain embodiments of the invention, M=Ni, R=trifluorobenzene and R'=hydrogen. In some embodiments of the invention, the one of more alpha-olefins is selected from the group alkenes having between three and ten carbon atoms.

The support can be any support containing —OH groups, including but not limited to, silica, porous silica, HCl treated glass, zeolites, partially hydrolyzed trimethylaluminum ("PHT"), and the like, and silica based supports may be preferred.

In certain embodiments of the invention, the ionic liquid comprises a salt selected from the group consisting of AlCl$_3$, AlRCl$_2$ and AlR$_2$Cl, where R is an alkyl chain. In some embodiments of the invention, the ionic liquid comprises a cation select from the group consisting of ammonium, imidazolium, sulfonium and phosphonium salts.

Certain embodiments of the invention provide the process wherein the alkylaluminum compound is chloroethylaluminum.

Other embodiments of the invention provide a process for the dimerization of olefins including: (a) modifying a support material containing —OH groups with an alkyaluminum compound to form a modified support material; (b) mixing an organometallic complex of the formula:

where M is selected from the group of Ti, Zr, Hg, Ni, and V and R and R' are selected from the group consisting of hydrogen, alkyl, aryl, alkenyl, alkynyl, alkyloxy, substituted aryl, and halogens with one or more co-catalysts selected from the group of methylaluminoxane (MAO) and $B(C_6F_5)_3$ to form a combined catalyst; and (c) mixing the combined catalyst with one or more alpha-olefins.

DESCRIPTION OF EMBODIMENTS OF THE INVENTION

In one embodiment of the invention, a process for dimerizing olefins utilizes an organometallic catalyst/co-catalyst composition having the formula:

where M is selected from the group of titanium, zirconium, mercury, nickel and vanadium, and R and R' are selected from the group of hydrogen, alkyl, aryl, alkenyl, alkynyl, alkyloxy, substituted aryl, and halogens to form a buffered ionic liquid/catalyst complex; (d) mixing the buffered ionic liquid/catalyst complex with the modified support material to form an immobilized buffered catalyst; and (e) mixing the immobilized buffered catalyst with one or more alpha-olefins.

In some embodiments of the invention, the organometallic compound is mixed with a co-catalysts. Appropriate co-catalysts include ionic liquids, which may be buffered and/or supported on solid supports. For example, support material containing OH groups may be modified with one or more aluminumhalide, alkylaluminumdihalide, and dialkylaluminumhalide or trialkylaluminum compounds (generically, "$AlX_nR_{3-n}$"). Generally, to achieve the support modification, the support material is mixed with a solution of the $AlX_nR_{3-n}$ with stirring. Suitable solvents include aromatics and paraffins having 5 or more carbon atoms, including by way of example, toluene, benzene, pentane, hexane, cyclohexane and dichloromethane.

Excess solvent may be removed following a reaction time from between about 2 minutes to about 30 minutes, preferably between about 5 and 25 minutes and most preferably between about 10 and about 20 minutes. The result is a coated support material. The equation below illustrates an exemplary formation of a modified support according to one embodiment of the invention.

The ionic liquid is primarily a salt or mixture of salts that melt below room temperature. In some embodiments of the invention, the ionic liquid salt may be one or more of aluminum halide, alkylaluminum halide, gallium halide or alkylgallium halide. Preferably, the ionic liquid salt is one or more of $AlCl_3$, $AlRCl_2$, or $AlR_2Cl$ where R is an alkyl chain. In some embodiments of the invention, the ionic liquid cation may be ammonium, imidazolium, sulfonium or phosphate salt. In preferred embodiments, the ionic liquid cation is selected from ammonium halides containing one or more alkyl moieties having from 1 to about 9 carbon atoms, for example, trimethylbenzylammoniumchloride, or hydrocarbonyl substituted imidazolium halides, for example, 1-buty1-3-methylimidazolium chloride.

In some embodiments of the invention, the ionic liquid is buffered. For example, a buffered system of ionic liquid may be produced utilizing one or more buffers having the general formula $R_4Al_2Cl_2$ or $R_2Al_2Cl_4$ where the neutral compounds are dissolved in an organic phase. For example:

$$2[Et_2Al_2Cl_5]^- \leftrightarrow 2[AlCl_4]^- + Et_4Al_2Cl_2$$

$$2[Et_2Al_2Cl_5]^- \leftrightarrow 2[AlCl_4]^- + Et_2Al_2Cl_4.$$

In some embodiments, the quarternary amine is dissolved first in methylene chloride and $AlCl_3$ and stirred between 1 and 20 hours. The solvent is then removed by any of a number of known methods, most preferably by vacuum. The buffered system is then formed by addition of about 0.001 to about 0.2 equivalents $Et_2AlCl$ to yield a ratio of the buffered system of amine: $AlCl_3$:$Et_2AlCl$ of about 1:1.22:0.2.

The ionic liquid which will be used in producing the novel catalyst composition may be produced by first separately dissolving each of an acceptable cation and an acceptable anion in a solvent. The dissolved cation and anion are then mixed followed by removal of solvent. The organometallic catalyst, for example of the formula above, is then mixed with the ionic liquid.

The immobilized buffered catalyst is then formed by mixing the organometallic catalyst/ionic liquid composition with the coated support material. Following sufficient mixing, excess solvent is removed, leaving an immobilized buffered catalyst solid or powder material. The immobilized buffered catalyst may then be mixed with one or more alpha-olefins to dimerize the olefins. In some embodiments, the immobilized buffered catalyst is mixed with a single alpha-olefin to form homogenous dimers or oligomers having fifty or fewer monomer units.

EXAMPLE 1

Silica modification: Commercially available silica (Davicat® SI 1102 from W.R. GRACE & CO®) is calcined at 400° C. in dry argon for 4 hours. The calcined silica (13.97 g) is slowly added to a 1 molar solution of $Et_2AlCl$ in toluene with vigorous stirring (45 ml, 3-3.5 ml per g of calcined silica) and further stirred for 10-20 minutes. The toluene solution is decanted and the silica washed 3 times with toluene.

Ionic liquid preparation: 20.89 g 1-butyl-3-methylimidazolium chloride ("[BMIM]Cl" 95%, BASF) are dissolved in $CH_2Cl_2$. 19.43 g $AlCl_3$ (1.22 mol. eq., Reagent plus, Sigma-Aldrich) is suspended in 100 ml $CH_2Cl_2$ and the suspension is slowly transferred to the solution of BMIMCl. This addition is exothermic. The methylene chloride solvent is removed by subjecting the mixture to vacuum, heated to 70° C. and left on high vacuum until no more bubbles are observed. The result is a viscous, slightly colored liquid.

Catalyst Preparation: 5 g of the ionic liquid are placed in a schlenk tube and 20 mg of the bis(phenoxyimin) Ni(II) complex are added and the mixture is stirred for a few seconds.

Figure 1:
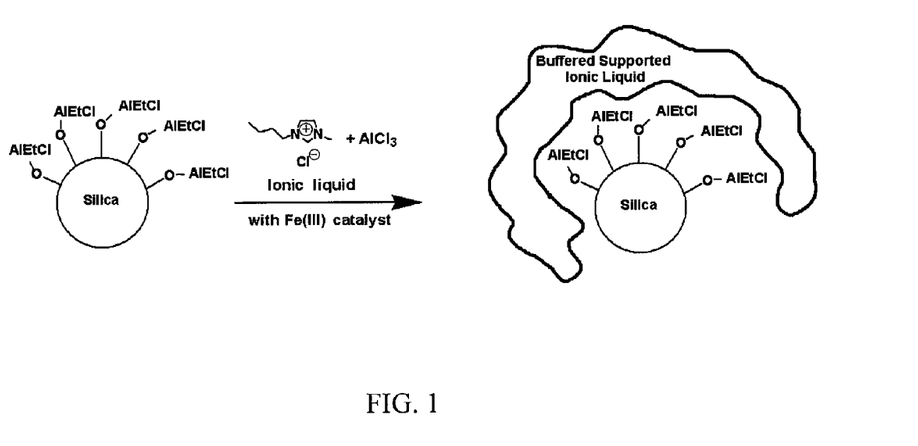
FIG. 1 is an equation showing the production of the immobilized buffered catalyst.

Catalyst coating: The toluene suspension of the coated support material (the complete amount of coated silica produced) is slowly added to 8.9 ml (80 wt %) of the catalyst containing ionic liquid with vigorous stirring. This mixture is stirred for 15 minutes to produce an immobilized buffered catalyst as shown in the equation found in FIG. 1. The toluene solvent is then decanted and the remainder of the toluene is removed by application of high vacuum to produce a powder.

Figure 2:
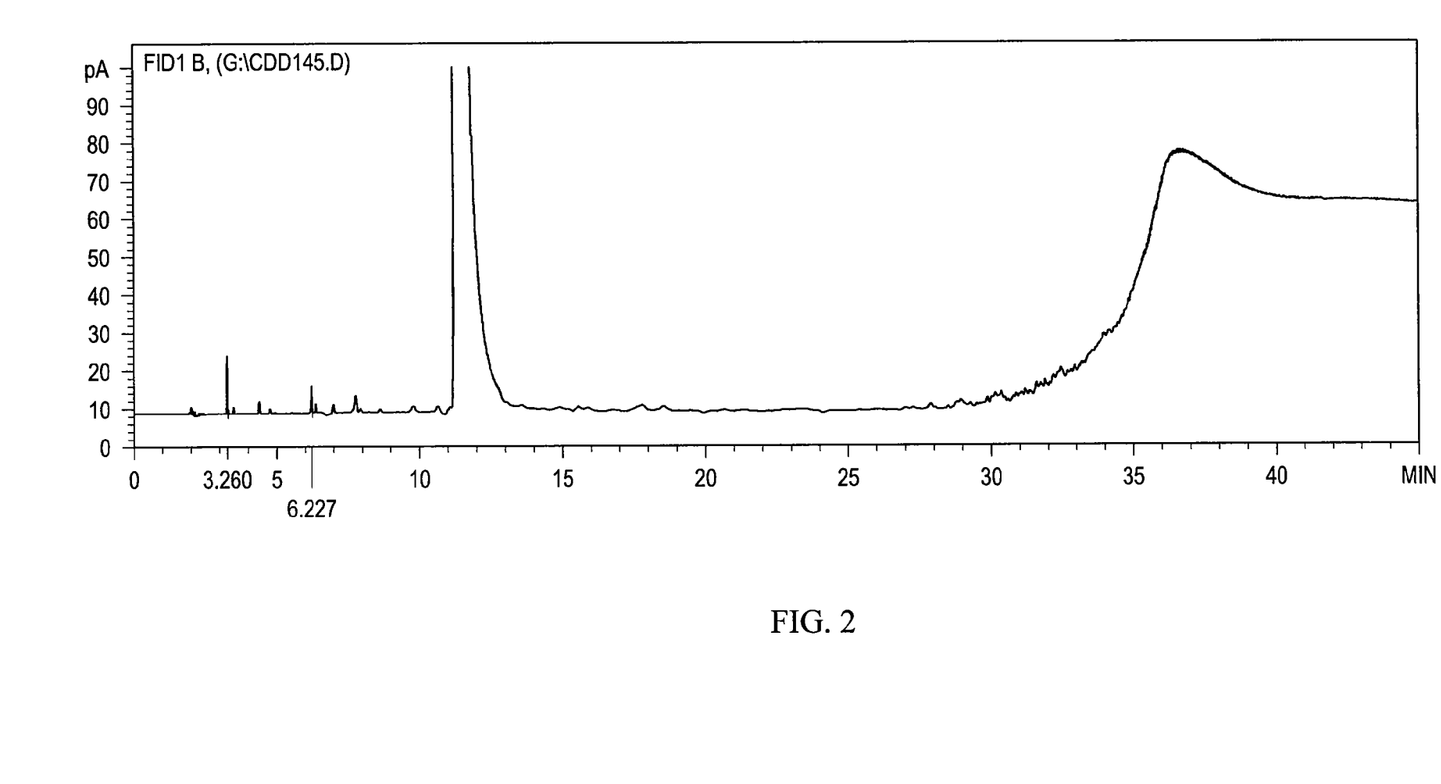
FIG. 2 is a gas chromatographic spectra of the results of the embodiment of the invention described in Example 1.

Dimerization of propene in a pressure schlenk tube: 5 g of the prepared catalyst (catalyst preparation [0018]) are placed in a pressure schlenk tube, a vacuum is applied and 50 ml of liquid propene (>99.3% purity 2.3) is condensed into the tube using liquid nitrogen. The schlenk tube is then placed in a room temperature water bath and stirred for 60 minutes. After the pressure is released, 19 g product remained in the schlenk tube, what equals about 554 kg Oligomer/mol×h. Gas chromatographic ("GC") analysis shown in FIG. 2 revealed a high-viscosity polyolefin content of over 90%.

Dimerization of propene in a fixed bed reactor: The remainder of the immobilized buffered powder catalyst (26.30 g) is loaded into a reactor tube. The reactor is run with a flow rate of 1 ml/min, 40° C., 20 bar, 20 wt % propene in pentane feed. Six samples were taken, each containing 94-96% dimers. Two cooled samples (dry ice, acetone+isopropanol) were taken revealing conversions of about 58% after 6 hours and about 14% after 12 hours.

In another embodiment of the invention, alpha olefins are homogenously dimerized using organometal complexes with selected co-catalysts. Specifically, oganometal complexes of the formula above may be mixed with one or more co-catalysts selected from the group of methylaluminoxane ("MAO") and $B(C_6F_5)_3$. The methylaluminoxane may be used in different ratios vis a vis the organometallic catalyst, ranging from about 1:100 to about 1:1000 catalyst:co-catalyst. Most preferably, MAO is used as a co-catalyst in a ratio between about 1:250 to about 1:750 catalyst:co-catalyst.

For the homogenous catalyzed reactions MAO (Methylalumoxane), $AlCl_3$, $AlR_3$, $AlR_2Cl$, $AlBu/AlCl_3$, $AlR_3/AlCl_3$, $AlR_2Cl/AlRCl_2$, where R=alkyl, aryl, alkenyl, alkynyl, are used. Additives such as but not limited to phosphoranes and amines may also be used. Without being bound by any particular theory, it is thought that by adding MAO, the cocatalyst activates the organometallic compound by generating a free coordination center by removing one ligand.

For the heterogeneous catalyzed reaction, the homogeneous activated complex is heterogenized on support material such as but not limited to silica gels, MgO, $Al_2O_3$, and such. Therefore, the catalyst is stirred together with the support for 20 minutes in a suitable solvent (for example, toluene) and can be used in a fixed bed reactor after removing the solvent.

EXAMPLE 2

Preparation of the ligand: In toluene 25 mmol (3.0 g) of Salicylaldehyde is mixed with 27.5 mmol (4.0 g) of a substituted aniline (2,4,5-trifluoroaniline) and a small amount of p-toluenesulfonic acid as catalyst. The solution is heated for reflux and stirred 2-6 hours using a water separator. The solution is filtered, the solvent is removed in vacuo and the product recrystallized in methanol.

Preparation of the complex: 10 mmol (2.5 g) of the respective ligand are dissolved in 150 ml of ethanol and stirred with 5 mmol (1.2 g) $Ni(OAc)_2 \cdot 4H_2O$ for two hours at 90° C. For purification the solution is concentrated in vacuo and the complex is precipitated with pentane and washed with pentane until the supernatant solution is clear and colorless. Drying the product in vacuo a green complex is obtained having the formula as shown above where R is trifluorobenzene and R' is hydrogen.

Figure 3:
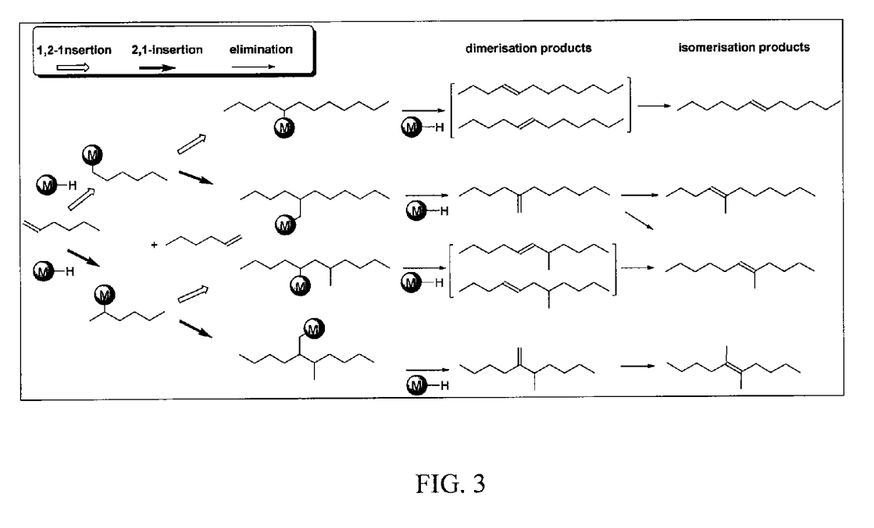
FIG. 3 is an equation illustrating the dimerization of alpha-hexene.

Dimerization: 15.0 mg of the organometallic complex is activated with 10.9 ml MAO (10% in toluene, Ni:Al=1:500). 15 ml of 1-hexene are added to 11 ml of the catalyst solution and the mixture is stirred for 5 hours at 0° C. Without being bound by any particular theory, the dimerization of alphahexene occurs as illustrated in the equation shown in FIG. 3.

Figure 4:
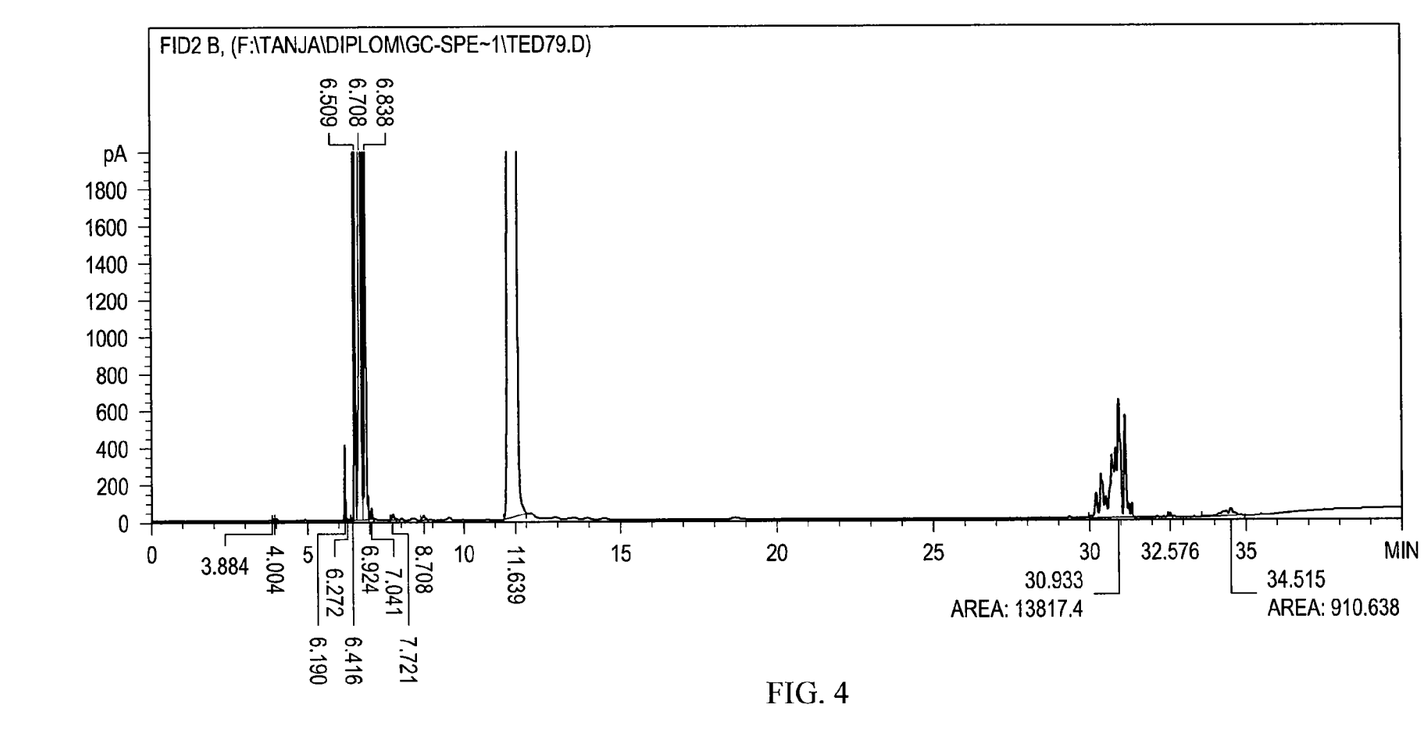
FIG. 4 is a GC spectra of the reaction products of the results of the embodiment of the invention described in Example 2.

The reaction products depend on 1,2- or 2,1-insertion and are able to isomerize. FIG. 4 illustrates a GC spectra of the reaction products after five hours. From 29.9-33.2 min dodecenes are detected, octadecenes are detected from 34.0-34.8 min and higher oligomers are detected after 36 minutes.

EXAMPLE 3

In some embodiments of the invention, the organometallic catalyst is immobilized on one or more supports selected from the group consisting of silica, zeolite and partially hydrolyzed trimethylaluminum ("PHT") and the like. Therefore, the activated catalyst is stirred together with the support material for 20 minutes in a suitable solvent (e.g., toluene) and can be used in a fixed bed reactor after removing the solvent.

Figure 5:
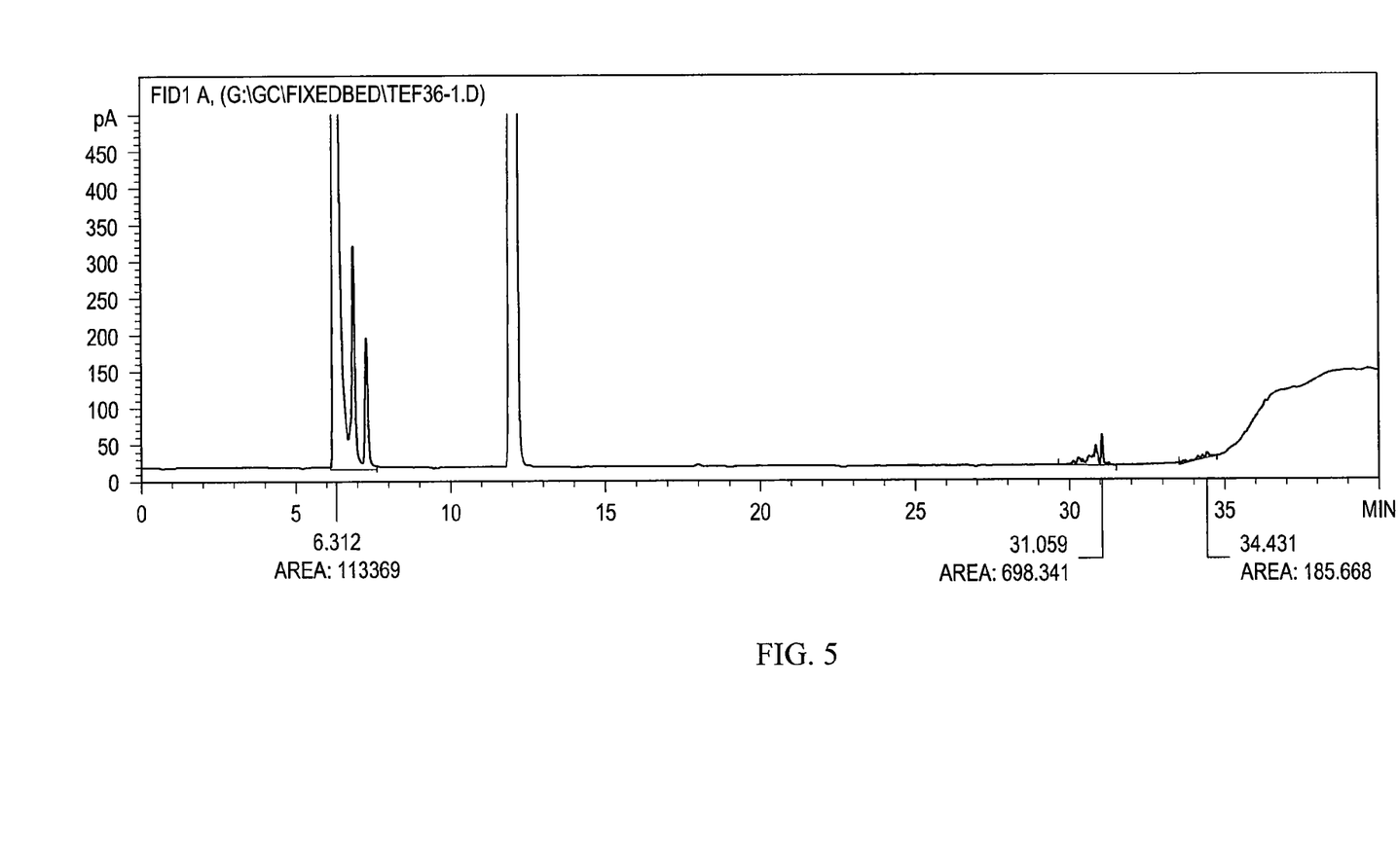
FIG. 5 is a GC spectra of the reaction products of the results of the embodiment of the invention described in Example 3.

The heterogenized catalyst is poured into the fixed bed tube and flowed with a 1-hexene/solvent mixture for 3 hours at room temperature. Toluene is used as solvent. Flow rate ranges between 0.5 and 1.0 ml/min. FIG. 5 shows the reaction products after one hour (flow rate 0.5 ml/min, 1-hexene:toluene=1:1).

General synthesis procedure for the silicagel/PHT catalyst system: At room temperature, 30 ml of a 2.0 M trimethylaluminum solution in toluene were added to a suspension of 2.0 g calcined silica gel in 100 ml toluene. 0.75 ml water was bubbled through the suspension as a moist argon flow. Thereupon, the reaction mixture heated itself to 60° C. After 10 min, the suspension became suddenly highly viscous. After cooling to room temperature, the mixture was stirred vigorously for 2 hours. Finally, 0.23 mmol of the catalyst precursor were added as solids and stirred for 5 min. Finally, the mixture was filtered and the solution dried in vacuo. The filtrate was colorless and contained no organic or inorganic components besides the solvent. Yields of the catalyst: 5.40 g (>95% calculated on aluminum content) of a powder colored according to the catalyst precursor.

What is claimed is:

1. A process for the dimerization of alpha-olefins comprising the steps of:
   modifying a support material containing —OH groups with an alkylaluminum compound to form a modified support material;
   mixing an ionic liquid having a melting point below about 70° C. with a buffer to form a buffered ionic liquid;
   mixing the buffered ionic liquid with an organometallic complex of the formula:

where M is selected from the group of Fe, Ti, Zr, Hg, and V and R and R' are selected from the group consisting of hydrogen, alkyl, aryl, alkenyl, alkenyl, alkyloxy, substituted aryl, and halogens to form a buffered ionic liquid/catalyst complex;
   mixing the buffered ionic liquid/catalyst complex with the modified support material to form an immobilized buffered catalyst; and
   mixing the immobilized buffered catalyst with one or more alpha-olefins.

2. The process of claim 1 wherein M=Fe, Ti, Zr, Hg and V, R=trifluorobenzene and R'=hydrogen.

3. The process of claim 1 wherein the one or more alpha-olefins is selected from the group alkenes having between three and ten carbon atoms.

4. The process of claim 1 wherein the support is silica, zeolite, partially hydrolyzed trimethylaluminum, or a mixture thereof.

5. The process of claim 1 wherein the ionic liquid comprises a salt selected from the group consisting of $AlCl_3$, $AlRCl_2$ and $AlR_2Cl$, where R is an alkyl chain.

6. The process of claim 1 wherein the ionic liquid comprises a cation selection from the group consisting of ammonium, imidazolium, sulfonium and phosphonium salts.

7. The process of claim 1 wherein the alkylaluminum compound is a chloroethylaluminum.

8. The process of claim 1 wherein the step of mixing the immobilized buffered catalyst with one or more alpha-olefins is conducted in a fixed bed reactor.

9. The process of claim 1 wherein the alpha-olefin dimerization reaction comprises 1,2- or 2,1- insertion.

10. The process of claim 1 further comprising drying the immobilized buffered catalyst to form a powder prior to the mixing of the immobilized buffered catalyst with one or more alpha-olefins.

11. The process of claim 1 wherein the alpha-olefin dimerization reaction comprises 1,2- or 2,1- insertion.

12. The process of claim 1 further comprising drying the immobilized buffered catalyst to form a powder prior to the mixing of the immobilized buffered catalyst with one or more alpha-olefins.

13. A process for the dimerization of alpha-olefins comprising the steps of:
   modifying a support material containing —OH groups with an alkylaluminum compound to form a modified support material;
   mixing an ionic liquid having a melting point below about 70° C. with a buffer to form a buffered ionic liquid;
   mixing the buffered ionic liquid with an organometallic complex of the formula:

where M=Ni, and R and R' are selected from the group consisting of hydrogen, alkyl, aryl, alkenyl, alkynyl, alkyloxy, substituted aryl, and halogens, and at least one of R and R'=alkyloxy to form a buffered ionic liquid/catalyst complex;
   mixing the buffered ionic liquid/catalyst complex with the modified support material to form an immobilized buffered catalyst; and
   mixing the immobilized buffered catalyst with one or more alpha-olefins.

14. The process of claim 13 wherein M=Ni, R=trifluorobenzene and R'=hydrogen.

15. The process of claim 13 wherein the one or more alpha-olefins is selected from the group alkenes having between three and ten carbon atoms.

16. The process of claim 13 wherein the support is silica, zeolite, partially hydrolyzed trimethylaluminum, or a mixture thereof.

17. The process of claim 13 wherein the ionic liquid comprises a salt selected from the group consisting of $AlCl_3$, $AlRCl_2$ and $AlR_2Cl$, where R is an alkyl chain.

18. The process of claim 13 wherein the ionic liquid comprises a cation selection from the group consisting of ammonium, imidazolium, sulfonium and phosphonium salts.

19. The process of claim 13 wherein the alkylaluminum compound is a chloroethylaluminum.

20. The process of claim 13 wherein the step of mixing the immobilized buffered catalyst with one or more alpha-olefins is conducted in a fixed bed reactor.

21. A process for the dimerization of olefins comprising the steps of:

modifying a support material containing —OH groups with an alkylaluminum compound to form a modified support material;

mixing an organometallic complex of the formula:

where M=Ni, and R and R' are selected from the group consisting of hydrogen, alkyl, aryl, alkenyl, alkynyl, alkyloxy, substituted aryl, and halogens, and at least one of R and R'=alkyloxy with one or more co-catalysts selected from the group of methylaluminoxane (MAO) and $B(C_6F_5)_3$ to form a combined catalyst;

combining the modified support material with the combined catalyst to form a supported combined catalyst; and mixing the supported combined catalyst with one or more alpha-olefins.

22. The process of claim 21 wherein the alkylaluminum compound is a chloroethylaluminum.

23. The process of claim 21 wherein the support is silica, zeolite, partially hydrolyzed trimethylaluminum, or a mixture thereof.

24. The process of claim 21 wherein the one or more alpha-olefins is selected from the group alkenes having between three and ten carbon atoms.

25. The process of claim 21 wherein the olefin dimerization is conducted in a fixed bed reactor.

* * * * *